United States Patent
Matsukawa et al.

(10) Patent No.: US 9,242,950 B2
(45) Date of Patent: Jan. 26, 2016

(54) METHOD FOR PREPARING A FATTY ACID DERIVATIVE

(75) Inventors: Tatsuya Matsukawa, Tokyo-to (JP);
Noriyuki Yamamoto, Tokyo-to (JP);
Ryuji Ueno, Montgomery, MD (US);
Hiroyuki Kotajima, Funabashi (JP);
Shunsuke Fukuya, Sanyoonoda (JP);
Michiharu Handa, Sanyoonoda (JP);
Katsuya Sakata, Sanyoonoda (JP)

(73) Assignees: R-TECH UENO, LTD., Tokyo (JP);
SUCAMPO AG, Zug (CH)

( * ) Notice: Subject to any disclaimer, the term of this patent is extended or adjusted under 35 U.S.C. 154(b) by 291 days.

(21) Appl. No.: 13/538,189

(22) Filed: Jun. 29, 2012

(65) Prior Publication Data

US 2013/0005995 A1    Jan. 3, 2013

Related U.S. Application Data

(60) Provisional application No. 61/503,742, filed on Jul. 1, 2011.

(51) Int. Cl.
*C07D 307/30*    (2006.01)
(52) U.S. Cl.
CPC .................................... *C07D 307/30* (2013.01)
(58) Field of Classification Search
CPC ............. C07C 405/00; A61K 31/5575; A61K 31/557; C07D 307/30
See application file for complete search history.

(56) References Cited

U.S. PATENT DOCUMENTS

| | | | |
|---|---|---|---|
| 5,739,161 A * | 4/1998 | Ueno | 514/530 |
| 7,321,057 B2 * | 1/2008 | Hirata et al. | 562/503 |
| 7,355,064 B2 * | 4/2008 | Hirata et al. | 560/121 |
| 2006/0036108 A1 | 2/2006 | Hirata et al. | |
| 2007/0185206 A1 * | 8/2007 | Hirata et al. | 514/573 |
| 2007/0232838 A1 * | 10/2007 | Iwabuchi et al. | 568/700 |
| 2008/0221331 A1 * | 9/2008 | Iwabuchi et al. | 546/137 |
| 2009/0124806 A1 * | 5/2009 | Iwabuchi et al. | 546/72 |
| 2010/0204489 A1 * | 8/2010 | Hirata et al. | 549/305 |

FOREIGN PATENT DOCUMENTS

| | | |
|---|---|---|
| EP | 1 775 296 A1 | 4/2007 |
| JP | 2006-45231 A | 2/2006 |

OTHER PUBLICATIONS

Zuidema, D.R., et al., Novel method of reducing ketones using sodium hydroxide n isopropanol, 2010, Synthetic Communication, vol. 40, issue 8, pp. 1187-1191.*
Shibuya, Masatoshi et al., "2-Azaadamantane N-Oxyl (AZADO) and 1-Me-AZADO: Highly Efficient Organocatalysts for Oxidation of Alcohols", Journal of the American Chemical Society, Jul. 2006, pp. 8412-8413, vol. 128, No. 26.
Plumb, J.B. et al., "2-Iodoxybenzoic acid", Chem. Eng. News, Jul. 16, 1990, p. 3.

* cited by examiner

*Primary Examiner* — Yate K Cutliff
(74) *Attorney, Agent, or Firm* — Sughrue Mion, PLLC

(57) ABSTRACT

A method for manufacturing a fatty acid derivative represented by formula (I) is provided:

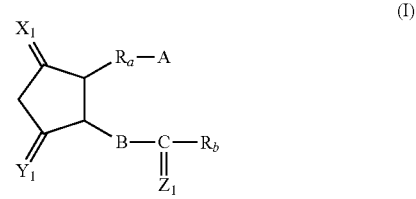

wherein $Z_1$ is

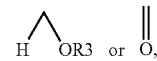

wherein R3 is a protecting group for a hydroxy group; which includes the step of reacting a compound of formula (II):

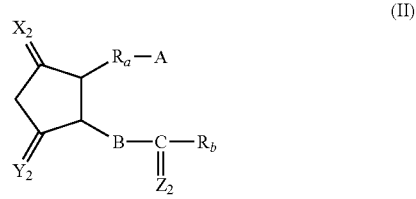

wherein $Z_2$ is the same as $Z_1$ except for when $Z_1$ is

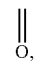

$Z_2$ is

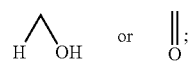

with a co-oxidizer under the presence of an azaadamantane-N-oxyl derivative.

6 Claims, No Drawings

METHOD FOR PREPARING A FATTY ACID DERIVATIVE

BACKGROUND OF THE INVENTION

Field of the Invention

The present invention relates to a novel method for manufacturing a fatty acid derivative that is useful as a medicament or a synthetic intermediate for a medicament.

Fatty acid derivatives are organic carboxylic acids existing in tissues and organs of human and the other mammals and have a wide variety of biological activity. Some fatty acid derivatives found in nature include those having, as a general structure thereof, a prostanoic acid skeleton as shown in the formula (A):

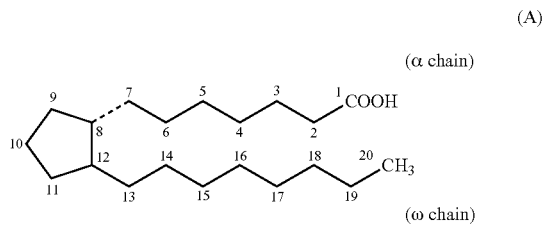 [SMILES: CCCCCCCCC1CCC[C@@H]1CCCCCCC(=O)O]

(A)

(α chain)

(ω chain)

In preparing the fatty acid derivative such as prostaglandin derivatives having the above prostanoic acid skeleton, oxidation of a hydroxy group is one of important reaction steps. Many methods to oxidize a hydroxy group have been known.

Swern oxidation that has been conventionally used for prostaglandin syntheses requires special manufacturing equipment that can operate at a very low reaction temperature (−70 to −40° C.). In addition, when the fatty acid derivative has a carboxyl group in the molecular, undesired by-product could be a major product due to side reactions (See, for example, US2006-0036108A, especially, comparative example 1, this document is herein incorporated by reference). In order to avoid this problem, protection of the carboxyl group before Swern oxidation and de-protection of the protecting group after the oxidation are needed, as a result, the manufacturing process become long and redundant by these additional steps.

The α position of the ketone obtained by the Swern oxidation could be substituted with chlorine and/or methylthio group by chloride and dimethylsulfonium ions generated from chloro dimethylsulfonium chloride, an active oxidative species, or reaction reagents (dimethylsulfoxide and oxalyl chloride) for Swern oxidation.

Especially, when the α position of the obtained ketone has high acidity, or the keto-structure tends to convert into enol-form, by-products like α-chloro derivative are easily generated.

Sometimes it is very difficult to remove the by-products like chloro or methylthio derivatives from the desired product by using a column chromatography. When/if the purification by crystallization is not very effective, crystallization has to be repeated. In addition, those by-products occasionally inhibit the reaction, especially catalytic hydrogenation and hydrogenolysis, in the following process steps to the final product. Furthermore, Swern oxidation co-generates dimethylsulfide that is strongly malodorous and therefore, equipment such as exhaust gas scrubber, activated carbon adsorption tower and the like are required for the malodor prevention.

Traditional oxidation method using heavy metal reagents such as chromic acid can be used for oxidation of compounds having carboxyl group. However, most of heavy metals are toxic and occasionally not suitable as an industrial production method for medicaments.

Dess-Martin oxidation also can be used to oxidize compounds having carboxyl group, however, the heat- and shock-sensitivity of this oxidizing reagent is reported Chem. Eng. News, Jul. 16, 3, 1990, this document is herein incorporated by reference.). In addition, this oxidizing reagent is not easily available as an industrial raw material from the market. Accordingly, Dess-Martin oxidation is not suitable for industrial manufacture.

TEMPO oxidation is also used for the oxidation of hydroxy groups. This reaction can be easily carried out under relatively mild conditions and therefore, without using equipment such as ultralow temperature reactor and exhaust gas scrubber. It has been known as a method that can produce the product with high purity and high production efficiency (US 2006-0036108A, this document is herein incorporated by references). However, some problems of TEMPO oxidation have been known to the art. For example, the oxidized form of TEMPO, i.e. the active form of TEMPO, is structurally instable and therefore, the reaction needs a relatively large amount of the catalyst. In addition, when a bulky substrate is oxidized using TEMPO, enough reactivity can hardly be achieved. In order to promote the reaction, 1.0-2.0 molar equivalent of halide salt such as sodium bromide, potassium bromide, tetrabutylammonium bromide or tetrabutylammonium chloride per one molar equivalent of the hydroxy group is usually added to the reaction. Those halide salts may, however, cause the generation of by-products such as a bromide analogue.

Under the above discussed circumstances, an industrially applicable method for oxidizing a hydroxy group that can suppress the generation of by-product has been desired.

SUMMARY OF THE INVENTION

An object of the present invention is to provide a new method for manufacturing a fatty acid derivative, which can be easily carried out under relatively mild conditions.

The instant inventors have intensively studied and found that a fatty acid derivative can be effectively produced by oxidizing a synthetic intermediate using co-oxidizer in the presence of an azaadamantane-N-oxyl derivative. According to the method of the present invention, the desired fatty acid derivative can be synthesized without special equipment, by using an easy-available inexpensive co-oxidizer and generation of the undesired by-product is suppressed.

Accordingly, the present invention provides a method for manufacturing a fatty acid derivative represented by formula (I):

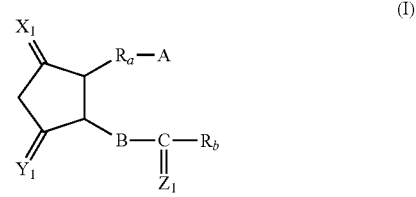

(I)

wherein $X_1$

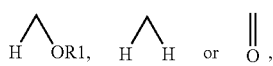

is wherein R1 is a protecting group for hydroxy group;
$Y_1$ is

wherein R2 is a protecting group for hydroxy group;
$Z_1$ is

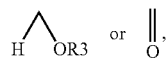

wherein R3 is a protecting group for hydroxy group,
provided that at least one of $X_1$, $Y_1$ and $Z_1$ is

A is —$CH_3$, —$CH_2OH$, —$COCH_2OH$, —COOH or a functional derivative thereof;
B is a single bond, —$CH_2$—, —$CH_2$—$CH_2$—, —CH=CH— or —C≡C—, —$CH_2$—$CH_2$—$CH_2$—, —CH=CH—$CH_2$—, —$CH_2$—CH=CH—, —C≡C—$CH_2$— or —$CH_2$—C≡C—;
Ra is bivalent saturated or unsaturated lower-medium aliphatic hydrocarbon group, which is unsubstituted or substituted by halogen atom, lower alkyl, lower alkoxy, oxo, aryl or heterocyclic group, provided that one or more carbon atoms of the aliphatic hydrocarbon group may optionally be replaced with oxygen, nitrogen or sulfur atom; and
Rb is hydrogen atom; saturated or unsaturated lower-medium aliphatic hydrocarbon group which is unsubstituted or substituted by a halogen, oxo, hydroxy, lower alkoxy, lower alkanoyloxy, cyclo(lower)alkyl, cyclo(lower)alkyloxy, aryl, aryloxy, heterocyclic or heterocyclic oxy; cyclo(lower)alkyl; cyclo(lower)alkyloxy; aryl; aryloxy; heterocyclic; or heterocyclic oxy,
which comprises the step of, reacting a compound of formula (II):

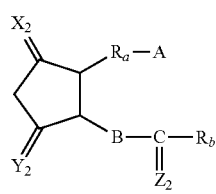

(II)

wherein, $X_2$ is the same as $X_1$ except for when $X_1$ is

$X_2$ is

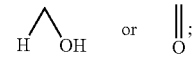

$Y_2$ is the same as $Y_1$ except for when $Y_1$ is

$Y_2$ is

$Z_2$ is the same as $Z_1$ except for when $Z_1$ is

$Z_2$ is

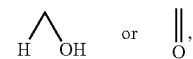

provided that at least one of $X_2$, $Y_2$ and $Z_2$ is

and, A, B, Ra and Rb are the same as above;
with a co-oxidizer under the presence of an azaadamantane N-oxyl derivative

DETAILED DESCRIPTION OF THE INVENTION in the definition of above Ra and Rb, the term "unsaturated" in the definitions for Ra and Rb is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower-medium aliphatic hydrocarbon" means a hydrocarbon having a straight or branched chain of 1 to 14 carbon atoms, wherein the side chain has preferably 1 to 3 carbon atoms. The preferred Ra has 1 to 10, more preferably, 6 to 10 carbon atoms, and the preferred Rb has 1 to 10, more preferably, 1 to 8 carbon atoms.

The term "halogen" includes fluorine, chlorine, bromine, and iodine atoms.

The term "lower" means a group having 1 to 6 carbon atoms unless otherwise specified.

The term "lower alkyl" means a straight- or branched-chain saturated hydrocarbon group having 1 to 6 carbon atoms, for example, methyl, ethyl, propyl, isopropyl, butyl, isobutyl, t-butyl, pentyl, and hexyl.

The term "lower alkoxy" means a lower alkyl-O— wherein the lower alkyl is as described above.

The term "lower alkanoyloxy" means a group represented by the formula RCO—O—, wherein RCO— is an acyl formed by oxidation of a lower alkyl as described above, for example, acetyl.

The term "lower cycloalkyl" means a group formed by cyclization of a lower alkyl group containing 3 or more carbon atoms as described above, for example, cyclopropyl, cyclobutyl, cyclopentyl, and cyclohexyl.

The term "cyclo(lower)alkyloxy" means a group represented by the formula cycloalkyl-O—, wherein cycloalkyl is described above.

The term "aryl" includes aromatic hydrocarbon rings (preferably monocyclic groups), which may be substituted, for example, phenyl, tolyl and xylyl. Examples of the substituents in this case include halogen, and halogen substituted lower alkyl group, wherein halogen atom and lower alkyl group are as described above.

The term "aryloxy" means a group represented by the formula ArO—, wherein Ar is an aryl group as described above.

The term "heterocyclic" includes mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen, oxygen and sulfur atoms. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolonyl, benzothiazolyl, phenothiazinyl. Examples of the substituent in this case include halogen, and halogen substituted lower alkyl group, wherein halogen atom and lower alkyl group are as described above.

The term "heterocyclic-oxy" means a group represented by the formula HcO—, wherein Hc is a heterocyclic group as described above.

The term "functional derivative" of A includes salts, preferably pharmaceutically acceptable salts, ethers, esters, and amides.

Examples of suitable "pharmaceutically acceptable salts" include nontoxic salts which are commonly used, and salts with inorganic bases, for example, alkali metal salts (sodium salt, potassium salt and the like); alkaline earth metal salts (calcium salt, magnesium salt and the like); ammonium salts; salts with organic bases, for example, amine salts (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, lysine salt, procaine salt, and caffeine salt); basic amino acid salts (such as arginine salt, and lysine salt); tetraalkyl ammonium salts and the like. These salts may be manufactured from, for example, corresponding acids and bases in accordance with a conventional manner or salt exchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester, and 1-cyclopropylethyl ester; lower alkenyl esters such as vinyl ester, and allyl ester; lower alkynyl esters such as ethynyl ester, and propynyl ester; hydroxy (lower)alkyl esters such as hydroxyethyl ester; and lower alkoxy(lower)alkyl esters such as methoxymethyl ester, and 1-methoxyethyl ester as well as, for example, optionally substituted aryl esters such as phenyl ester, tosyl ester, t-butylphenyl ester, salicyl ester, 3,4-dimethoxyphenyl ester, and benzamidophenyl ester; and aryl(lower)alkyl esters such as benzyl ester, trityl ester, and benzhydryl ester.

An amide for A is a group represented by formula: —CONR'R", wherein R' and R" independently represent hydrogen atom, lower alkyl, aryl, alkyl- or aryl-sulfonyl, lower alkenyl or lower alkynyl. Examples of amides include mono- or di-lower alkyl amides such as methylamide, ethylamide, and dimethylamide; aryl amides such as anilide, and toluidide; and alkyl- or aryl-sulfonyl amides such as methylsulfonyl amide, ethylsulfonyl amide, and tolylsulfonyl amide.

Preferred examples of A include —COOH, and a pharmaceutically acceptable salt, an ester and an amide thereof.

Preferred B is —$CH_2$—$CH_2$— which provides the structure of so-called, 13,14-dihydro type derivative.

Preferred Ra is a hydrocarbon having 1-10 carbon atoms, more preferably, 6-10 carbon atoms. One or more carbon atom of the hydrocarbon group may optionally be replaced with oxygen, nitrogen or sulfur atom.

Examples of Ra include, for example, the following groups:
—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—CH($CH_3$)—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$—)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—$CH_2$—CH($CH_3$)—$CH_2$—, Preferred Rb is a hydrogen atom or a hydrocarbon containing 1-10 carbon atoms, more preferably, 1-8 carbon atoms that is substituted by halogen atom such as fluorine.

In the specification and claims, the term "protecting group for hydroxy group" means a functional group which is introduced to protect the hydroxy group from oxidation. In the present invention, the protecting group may be any group as long as it can act as such. Examples of the protecting groups may include methyl, methoxymethyl, ethyl, 1-ethoxyethyl, benzyl, substituted benzyl, allyl, tetrapyranyl, t-butyldimethylsilyl, triethylsilyl, triisopropylsilyl, diphenylmethylsilyl, formyl, acetyl, substituted acetyl, benzoyl, substituted benzoyl, methyloxycarbonyl, benzyloxycarbonyl, t-buthloxycarbonyl and allyloxycarbonyl groups.

Examples of azaadamantane-N-oxyl derivatives that can be used in the present invention include, but are not limited to, 2-azaadamantane-N-oxyl (AZADO) and 1-methyl-2-azaadamantane-N-oxyl (1-Me-AZADO). The azaadamantane-N-oxyl derivative also includes chemical substances generating the same chemical species as an active oxidative species obtained from 2-azaadamantane-N-oxyl (AZADO), 1-methyl-2-azaadamantane-N-oxyl (1-Me-AZADO), or the like, by use of a co-oxidizer in a reaction system. Examples thereof include, but are not limited to, 2-hydroxy-2-azaadamantane (AZADOL [registered trademark of Nissan Chemical Industries, Ltd.]), 2-hydroxy-1-methyl-2-azaadamantane (1-Me-AZADOL), and the like.

The amount of the azaadamantane-N-oxyl derivative used in the reaction may be about 0.0005-1.0 mole, preferably about 0.001-0.1 mole per one mole of the starting compound to be oxidized or a compound of formula (II).

The co-oxidizer used in the present invention is one which can convert (i) the azaadamantane-N-oxyl derivative into an active oxidative species thereof; (ii) a reduced form of azaadamantane derivative (for example, 2-hydroxy-2-azaadamantane), which is generated upon oxidation of a, into the active oxidative species, as shown in the following scheme. Examples of co-oxidizers may include hypohalogenous acid such as hypochlorous acid or a salt thereof, halogenous acid such as bromous acid or a salt thereof, compounds having polyvalent iodine such as iodobenzene acetate, peroxides such as 3-chloro-perbenzoidc acid, N-halogen substituted succinimides such as N-chloro succinimide.

Catalytic Cycle and Action of Co-Oxidizer (for Example, Sodium Hypochlorite)

The amount of the co-oxidizer in the reaction may be 1.0-3 molar equivalents, preferably 1.1-2 molar equivalents and more preferably 1.1-1.5 molar equivalents per one molar equivalent of the hydroxy group to be oxidized.

The reaction may be conducted in an organic solvent, an aqueous solvent, a mixture thereof, or a two-phase solvent system consisting of an organic and an aqueous solvents.

Examples of organic solvents used in the present invention may be aromatic hydrocarbon solvent such as toluene, aliphatic hydrocarbon solvent such as hexane, halogen-containing solvent such as dichloromethane, ketones such as acetone, esters such as ethyl acetate.

The aqueous solvent may contain a pH adjusting agent such as sodium hydrogen carbonate, pH buffer such as potassium dihydrogen phosphate and sodium dihydrogen phosphate.

According to the present invention, a halide salt such as sodium bromide, potassium bromide, tetrabutylammonium bromide, and tetrabutylammonium chloride may be added to the reaction in order to facilitate the reaction.

The amount of the halide salt to be added is not limited and may be about 0.05-0.5 molar equivalents per one molar equivalent of the hydroxy group to be oxidized. In contrast, when TEMPO (tetramethylpiperidine-1-oxyl) is used instead of azaadamantane-N-oxyl derivative, 1.0-2.0 molar equivalents of TEMPO per one molar equivalent of the hydroxy group to be oxidized are required.

According to the present invention, the reaction may be carried out at a temperature of –10 to 50° C., preferably, about 0 to 20° C.

The present invention will be illustrated in more detail by way of the following examples. These examples should not be used as any limitation of the present invention.

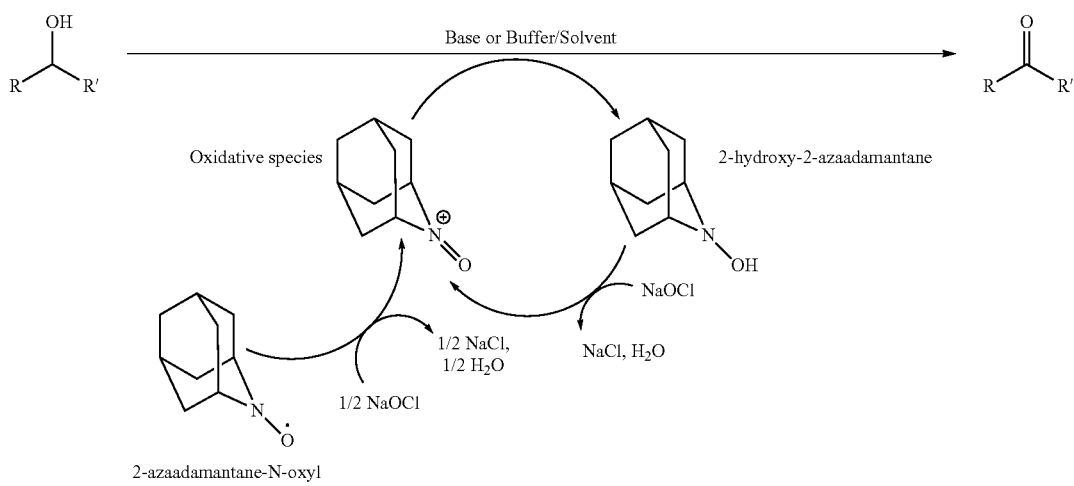

Example 1

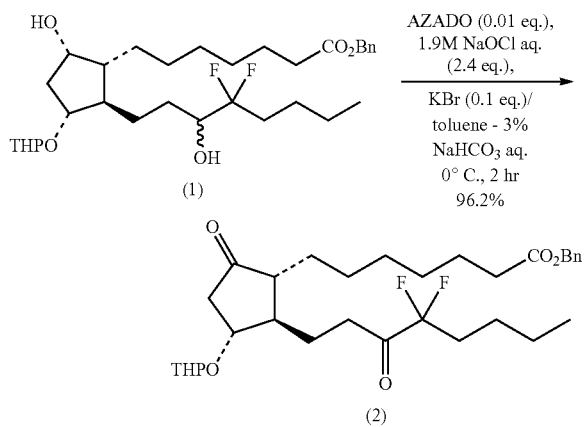

An alcohol compound (1) 0.210 g (0.37 mmol) was dissolved in toluene 1.5 ml, and AZADO (2 mg/ml in toluene 0.3 ml, 0.0037 mmol) was added thereto. The mixture was cooled in an ice bath to 0° C. Three percent aqueous sodium hydrogen carbonate 2.19 ml (0.74 mmol) and potassium bromide 4.4 mg (0.037 mmol) were added thereto. Then, about 1.9M aqueous sodium hypochlorite 0.47 ml (0.89 mmol) was added dropwise to the reaction, and the mixture was stirred for 2 hours. The reaction mixture was then added with saturated aqueous sodium thiosulfate, and the mixture was extracted three times with ethyl acetate. The extract was washed with dilute hydrochloric acid, saturated aqueous sodium hydrogen carbonate and then, brine, dried with anhydrous magnesium sulfate, filtered and concentrated under reduced pressure. The residue was purified with silica gel flash chromatography (column: BW-300SP 60 g, ethyl acetate-hexane 1:2) to give compound (2) as colorless oil. Yield 0.2006 g (96.2%).

$^1$H-NMR (400 MHz in CDCl$_3$, TMS=0 ppm) δ: 0.92 (3H, t, J=7.1 Hz), 1.20-2.38 (27H, m), 2.35 (2H, t, J=7.5 Hz), 2.68-3.05 (3H, m), 3.47-3.55 (1H, m), 3.78-3.91 (1.5H, m), 4.15 (0.5H, q, J=7.4 Hz), 4.58-4.59 (0.5H, m), 4.67-4.69 (0.5H, m), 5.11 (2H, s), 7.29-7.39 (5H, m).

Example 2

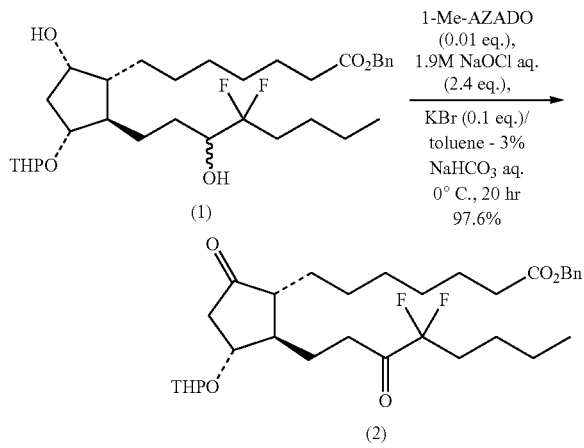

An alcohol compound (1) 0.210 g (0.37 mmol) was dissolved in toluene 1.5 ml, and 1-Me-AZADO (2 mg/ml in toluene 0.3 ml, 0.0037 mmol) was added thereto. The mixture was cooled in an ice bath to 0° C. Three percent aqueous sodium hydrogen carbonate 2.19 ml (0.74 mmol) and potassium bromide 4.4 mg (0.037 mmol) were added thereto. Then, about 1.9M aqueous sodium hypochlorite 0.47 ml (0.89 mmol) was added dropwise to the reaction, and the mixture was stirred for 20 hours. The reaction mixture was treated and purified in the similar manner as Example 1 to give compound (2) as colorless oil. Yield 0.2036 g (97.6%).

$^1$H-NMR (400 MHz in CDCl$_3$, TMS=0 ppm) δ: 0.92 (3H, t, J=7.2 Hz), 1.20-2.38 (27H, m), 2.35 (2H, t, J=7.5 Hz), 2.68-3.05 (3H, m), 3.47-3.54 (1H, m), 3.78-3.91 (1.5H, m), 4.15 (0.5H, q, J=7.4 Hz), 4.58-4.59 (0.5H, m), 4.67-4.69 (0.5H, m), 5.11 (2H, s), 7.30-7.39 (5H, m)

Example 3

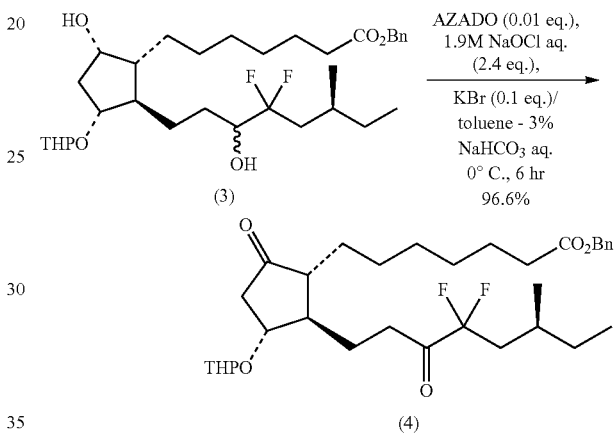

An alcohol compound (3) 0.200 g (0.34 mmol) was dissolved in toluene 1.4 ml, and AZADO (2 mg/ml in toluene 0.25 ml, 0.0034 mmol) was added thereto. The mixture was cooled in an ice bath to 0° C. Three percent aqueous sodium hydrogen carbonate 2.04 ml (0.69 mmol) and potassium bromide 4.1 mg (0.034 mmol) were added thereto. Then, about 1.9M aqueous sodium hypochlorite 0.43 ml (0.82 mmol) was added dropwise to the reaction, and the mixture was stirred for 6 hours. The reaction mixture was treated and purified in the similar manner as Example 1 to give benzyl 7[(1R,2R,3R)-2-((6S)-4,4-difluoro-6-methyl-3-oxooctyl)-5-oxo-3-(tetrahydro-2H-pyran-2-yloxy)cyclopentyl]heptanoate (4) as colorless oil. Yield 0.1919 g (96.6%).

$^1$H-NMR (400 MHz in CDCl$_3$, TMS=0 ppm) δ: 0.88 (3H, t, J=7.4 Hz), 0.97 (3H, d, J=6.5 Hz), 1.20-2.38 (26H, m), 2.35 (2H, t, 2.68-3.03 (3H, m), 3.47-3.54 (1H, m), 3.78-3.91 (1.5H, m), 4.13 (0.5H, q, J=7.4 Hz), 4.58-4.59 (0.5H, m), 4.67-4.69 (0.5H, m), 5.11 (2H, s), 7.30-7.39 (5H, m)

Example 4

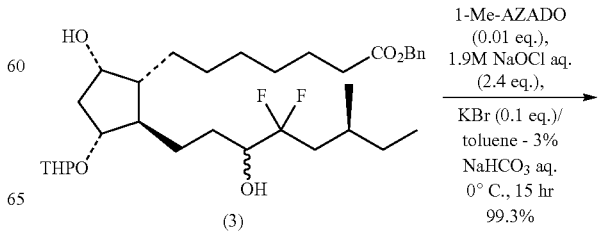

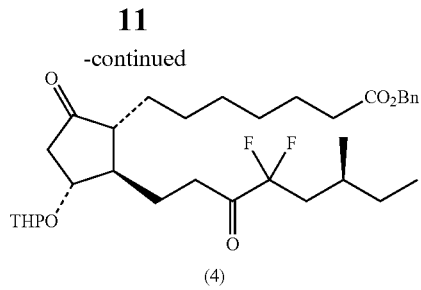

(4)

An alcohol compound (3) 0.200 g (0.34 mmol) was dissolved in toluene 1.4 ml, and 1-Me-AZADO (2 mg/ml in toluene 0.25 ml, 0.0034 mmol) was added thereto. The mixture was cooled in an ice bath to 0° C. Three percent aqueous sodium hydrogen carbonate 2.04 ml (0.69 mmol) and potassium bromide 4.1 mg (0.034 mmol) were added thereto. Then, about 1.9M aqueous sodium hypochlorite 0.43 ml (0.82 mmol) was added dropwise to the reaction, and the mixture was stirred for 15 hours. The reaction mixture was treated and purified in the similar manner as Example 1 to give benzyl 7-[(1R,2R,3R)-2-((6S)-4,4-difluoro-6-methyl-3-oxooctyl)-5-oxo-3-(tetrahydro-2H-pyran-2-yloxy)cyclopentyl]heptanoate (4) as colorless oil. Yield 0.1973 g (99.3%).

$^1$H-NMR (400 MHz in CDCl$_3$, TMS=0 ppm) δ: 0.88 (3H, t, J=7.4 Hz), 0.97 (3H, d, J=6.1 Hz), 1.20-2.38 (26H, m), 2.35 (2H, t, J=7.5 Hz), 2.68-3.05 (3H, m), 3.47-3.54 (1H, m), 3.78-3.91 (1.5H, m), 4.15 (0.5H, q, J=7.4 Hz), 4.58-4.59 (0.5H, m), 4.67-4.69 (0.5H, m), 5.11 (2H, s), 7.29-7.39 (5H, m)

combined, washed twice with saturated aqueous sodium chloride (351 ml), and dried with anhydrous magnesium sulfate (55 g). After concentration under reduced pressure, the residue was purified by silica gel column chromatography (Fuji Silysia BW-300: 2110 g; ethyl acetate:hexane=1:4 to 1:2). The fractions containing impurities were re-purified by silica gel column chromatography (Fuji Silysia BW-300: 850 g; ethyl acetate:hexane=1:4 to 1:2) to give methyl 7-[(1R,2R,3R,5S)-5-acetoxy-2-((E)-(6S)-4,4-difluoro-6-methyl-3-oxo-1-octenyl)-3-(2-tetrahydropyranyloxy)cyclopentyl]heptanate (C) (75.03 g; 137.8 mmol; yield: 85.8%) as a pale yellow oil.

$^1$H-NMR (200 MHz, CDCl$_3$): δ (ppm): 0.88 (3H, t, J=7.3 Hz), 0.97 (3H, t, J=6.4 Hz), 2.07 (3H, s), 2.15-1.03 (23H, m), 2.28 (2H, t, J=7.5 Hz), 2.87-2.36 (2H, m), 3.50-3.31 (1H, m), 3.66 (3H, s), 3.88-3.60 (1H, m), 4.19-3.93 (1H, m), 4.61-4.46 (1H, m), 5.19-5.09 (2H, m), 6.63 (0.5H, d, J=15.6 Hz), 6.68 (0.5H, d, J=15.6 Hz), 7.05 (0.5H, dd, J=15.6, 7.0 Hz), 7.10 (0.5H, dd, J=15.6, 6.5 Hz).

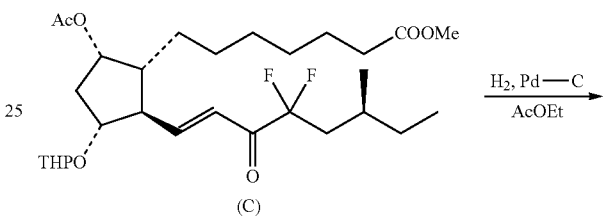

(C)

Synthesis of alcohol compound (3)

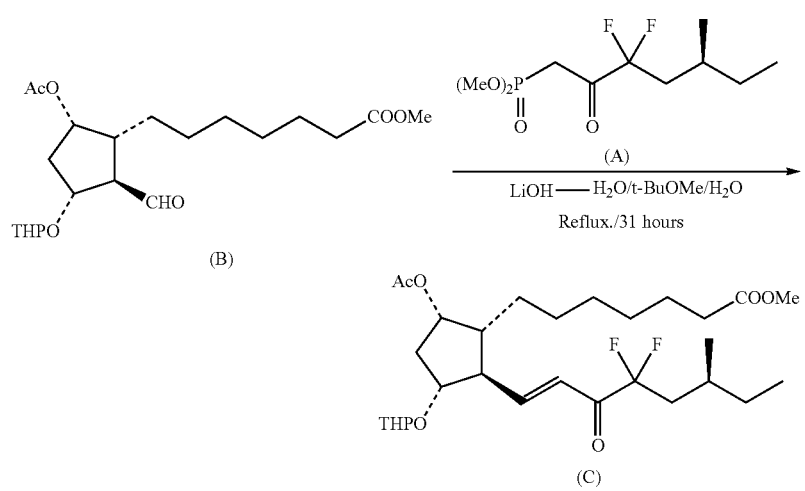

To a solution of dimethyl ((5S)-3,3-difluoro-5-methyl-2-oxoheptyl)phosphonate (A) (74.7 g, 274 mmol) in t-butyl methyl ether (1120 ml), lithium hydroxide monohydrate (11.5 g, 273 mmol) was added and the mixture was stirred for one hour at room temperature. A solution of methyl 7-[(1R, 2R,3R,5S)-5-acetoxy-2-formyl-3-(2-tetrahydropyranyloxy)cyclopentyl]heptanate (B) (64.02 g, 160.6=1) in t-butyl methyl ether (278 ml) and water (21.7 ml) were added thereto, and the mixed solution was heat refluxed for approximately 31 hours (internal temperature: approximately 53° C.). After cooling to room temperature, water (351 ml) was added to the solution and the mixture was stirred, let to stand and then separated into two layers. The aqueous layer was extracted twice with ethyl acetate (234 ml). The organic layers were

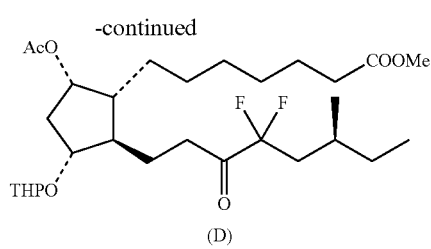

(D)

To a solution of methyl 7-[(1R,2R,3R,5S)-5-acetoxy-2-((E)-(6S)-4,4-difluoro-6-methyl-3-oxo-1-octenyl)-3-(2-tetrahydropyranyloxy)cyclopentyl]heptanate (C) (76.78 g, 141.0 mmol) in ethyl acetate (357 ml), 5%-palladium on carbon (7.30 g) was added and the solution was hydrogenated at room temperature and the ambient pressure. The reaction mixture was filtered, the filtrate was concentrated under reduced pressure to give methyl 7-[(1R,2R,3R,5S)-5-acetoxy-2-((6S)-4,4-difluoro-6-methyl-3-oxooctyl)-3-(2-tetrahydropyranyloxy)cyclopentyl]heptanate (D) (72.69 g; 133.0 mmol; yield: 94.3%) as a colorless oil.

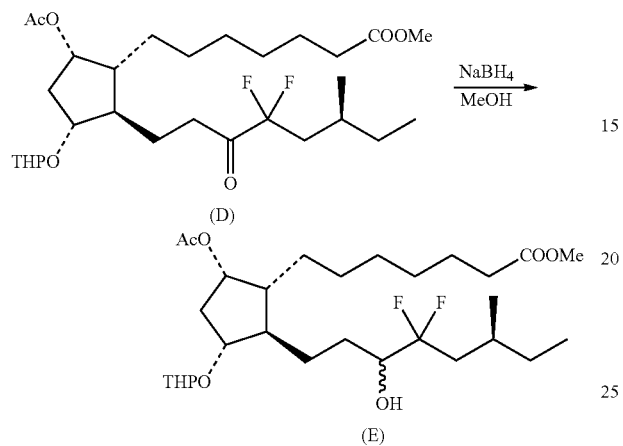

A solution of methyl 7-[(1R,2R,3R,5S)-5-acetoxy-2-((6S)-4,4-difluoro-6-methyl-3-oxooctyl)-3-(2-tetrahydro pyranyloxy)cyclopentyl]heptanate (D) (72.56 g, 132.7=1) in methanol (290 ml) was cooled to approximately −20° C., and sodium borohydride (5.00 g, 132.2 mmol) was added thereto. After stirring for approximately 35 minutes, acetic acid (7.5 ml, 131=1) was added dropwise, and the reaction mixture was concentrated under reduced pressure. The residue was supplemented with water (326 ml) and extracted three times with ethyl acetate (226 ml). The organic layers were combined, washed with 3% aqueous sodium chloride (323 ml) and saturated aqueous sodium chloride (323 ml), and dried with anhydrous magnesium sulfate (40.6 g). The solution was concentrated under reduced pressure to give methyl 7-[(1R,2R,3R,5S)-5-acetoxy-2-((6S)-4,4-difluoro-6-methyl-3-hydroxyoctyl)-3-(2-tetrahydropyranyloxy)cyclopentyl]heptanate (E) (73.01 g; quantitative yield) as a colorless oil.

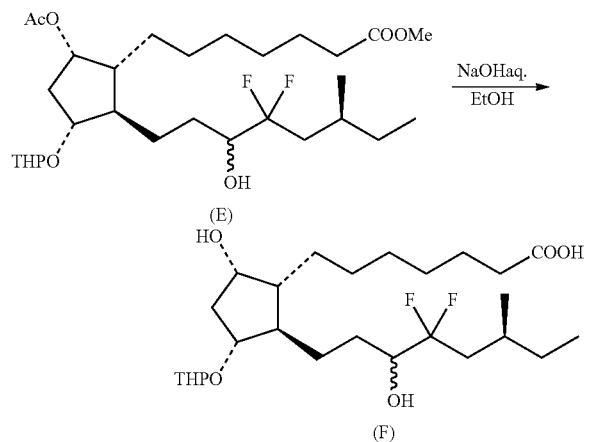

A solution of methyl 7-[(1R,2R,3R,5S)-5-acetoxy-2-((6S)-4,4-difluoro-6-methyl-3-hydroxyoctyl)-3-(2-tetrahydropyranyloxy)cyclopentyl]heptanate (E) (132.5 mmol) in ethanol (213 ml) was cooled on ice, and an 24% sodium hydroxide aqueous solution (135 ml, 1029 mmol) was added thereto dropwise. After stirring at room temperature for approximately 3.5 hours, the reaction mixture was concentrated under reduced pressure. The residue was mixed with water (281 ml) and t-butyl methyl ether (141 ml), and cooled on ice. After 6M-hydrochloric acid was added dropwise to adjust to pH 3 to 4, the solution was extracted three times with ethyl acetate (281 ml). The organic layers were combined and sequentially washed with water (281 ml) twice and saturated aqueous sodium chloride (338 ml). After drying with anhydrous magnesium sulfate (50 g), the solution was concentrated under reduced pressure to give crude 7[(1R,2R,3R,5S)-2-((6S)-4,4-difluoro-6-methyl-3-hydroxyoctyl)-5-hydroxy-3-(2-tetrahydropyranyloxy)cyclopentyl]heptanoic acid (F) as white solid. The entire amount was used in the following step without purification.

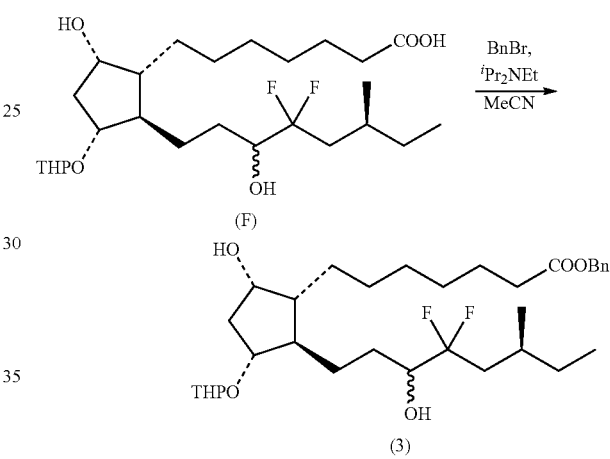

To the crude 7-[(1R,2R,3R,5S)-2-((6S)-4,4-difluoro-6-methyl-3-hydroxyoctyl)-5-hydroxy-3-(2-tetrahydropyranyloxy)cyclopentyl]heptanoic acid (F) in acetonitrile (319 ml), diisopropyl ethylamine (68.9 ml, 368 mmol) and benzyl bromide (46.7 ml, 366 mmol) were added and the mixture was stirred for about 13.5 hours at room temperature. The reaction mixture was concentrated under reduced pressure, ethyl acetate (369 ml) and water (283 ml) were added to the residue and the mixture was stirred, let to stand and then separated into two layers. The aqueous layer was extracted twice with ethyl acetate (226 ml). The organic layers were combined and washed with 1M-hydrochloric acid (339 ml), saturated sodium bicarbonate water (339 ml) and saturated aqueous sodium chloride (339 ml). After drying with anhydrous magnesium sulfate (50 g), the solution was concentrated under reduced pressure. The concentration residue was purified by silica gel column chromatography (Fuji Silysia BW-300: 2400 g; ethyl acetate:hexane=1:2) to give benzyl 7-[(1R,2R,3R,5S)-2-((6S)-4,4-difluoro-3-hydroxy-6-methyloctyl)-5-hydroxy-3-(tetrahydro-2H-pyran-2-yloxy)cyclopentyl]heptanoate (3) (76.16 g; 130.7 mmol; yield: 98.7%) as a colorless oil.

$^1$H-NMR (200 MHz, CDCl$_3$): δ (ppm): 0.88 (3H, t, J=7.5 Hz), 0.98 (3H, d, J=6.2 Hz), 1.21-2.47 (30.5H, m), 2.35 (2H, t, J=7.5 Hz), 2.81 (0.5H, d, J=6.4 Hz), 3.46-4.14 (5H, m), 4.61-4.66 (1H, m), 5.11 (2H, s), 7.30-7.39 (5H, m).

Example 5

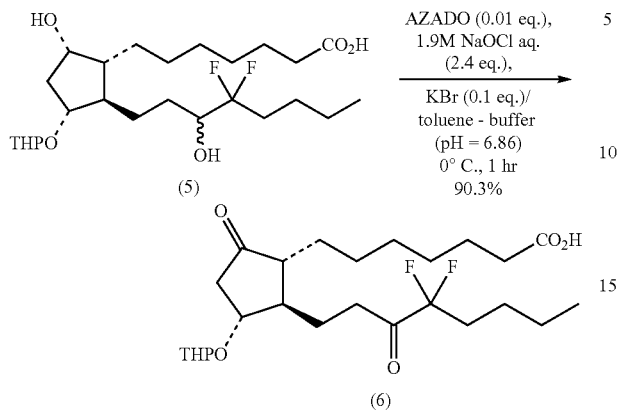

An alcohol compound (5) 0.233 g (0.49 mmol) was dissolved in toluene 1.6 ml, and AZADO in toluene (2 mg/ml in toluene 0.35 ml, 0.0049 mmol) was added thereto. The mixture was cooled in an ice bath to 0° C. Neutral phosphate buffered solution (2.0 ml), potassium bromide 5.8 mg (0.049 mmol) were added thereto. Then, about 1.9M aqueous sodium hypochlorite 0.62 ml (1.17 mmol) was added dropwise to the reaction, and the mixture was stirred for 1 hour at 0° C. The reaction mixture was treated and purified in the similar manner as Example 1 to give compound (6) as colorless oil. Yield 0.2089 g (90.3%).

$^1$H-NMR (400 MHz in CDCl$_3$, TMS=0 ppm) δ: 0.93 (3H, t, J=7.2 Hz), 1.22-2.38 (28H, m), 2.34 (2H, t, J=7.6 Hz), 2.69-3.05 (3H, m), 3.48-3.56 (1H, m), 3.79-3.92 (1.5H, m), 4.15 (0.5H, q, J=7.3 Hz), 4.59-4.60 (0.5H, m), 4.68-4.70 (0.5H, m).

Example 6

An alcohol compound (7) 0.200 g (0.50 mmol) was dissolved in dichloromethane 1.4 ml, AZADO in toluene (2 mg/ml in toluene, 0.2 ml, 0.0025 mmol) and then, [bis(acetoxy)iodo]benzene (BAIB) 0.1769 g (0.549 mmol) were added to the mixture. The mixture was stirred for 5 hours at room temperature. The reaction mixture was treated and purified in the similar manner as Example 1 to give compound (8) as colorless oil. Yield 0.1900 g (95.5%).

$^1$H-NMR (400 MHz in CDCl$_3$, TMS=0 ppm) δ: 1.19-2.18 (18H, m), 2.07 (3H, s), 2.29 (2H, t, J=7.5 Hz), 2.32-2.43 (1H, m), 2.81-3.01 (1H, m), 3.41-3.50 (1H, m), 3.66 (3H, s), 3.76-3.83 (1H, m), 4.36-4.46 (1H, m), 4.54-4.60 (1H, m), 5.11-5.17 (1H, m), 9.78 (1H, dd, J=3.1, 20.9 Hz)

Comparative Example 1

Swern Oxidation

Oxalyl chloride 56.9 ml (652 mmol) in dichloromethane (634 ml) was cooled in a dry-ice/methanol bath. dimethyl sulfoxide (DMSO) 92.5 ml (1303 mmol) was added dropwise thereto and the mixture was stirred for 30 minutes. Benzyl 7-[(1R,2R,3R,5S)-2-(4,4-difluoro-3-hydroxyoctyl)-5-hydroxy-3-(2-tetrahydropyranyloxy)cyclopentyl]heptanate (1) (74.21 g, 130.5 mmol) in dichloromethane (198 ml) was added dropwise to the mixture and the mixture was stirred for 1.5 hours. After that, triethylamine 273 ml (1959 mmol) was added dropwise to the reaction mixture with stirring and the reaction mixture was warmed to 0° C. Saturated aqueous ammonium chloride (594 ml) was then added to the reaction. The reaction mixture was stirred and then, stood still and separated. The aqueous phase was extracted twice with dichloromethane. The combined organic phase was washed successively with 0.1N hydrochloric acid (594 ml), water (594 ml), saturated sodium bicarbonate water (594 ml) and then, saturated aqueous sodium chloride (594 ml). The mixture was dried over anhydrous magnesium sulfate (48 mg), and concentrated under reduced pressure. The residue was dissolved in an appropriate amount of ethyl acetate/hexane (1:10) mixed solvent and the insoluble material was filtered out. The filtrate was evaporated and purified with silica gel column chromatography (BW-300 Fuji Silysia Chemical Ltd, 2260 g, ethyl acetate-hexane 1:4) to give Benzyl 7-[(1R,2R, 3R)-2-(4,4-difluoro-3-oxyoctyl)-5-oxy-3-(2-tetrahydropyranyloxy)cyclopentyl]heptanate (2). Yield 69.22 g, 122.6 mmol, 95.3%.

Comparative Test Example

The impurities in the products obtained in Example 1 and Comparative Example 1 were examined. 14-methylthio and 14-chloro analogues of the ketone compound (2) are generated by Swern oxidation. The amount of those impurities were determined. The results are shown in the table 1 below:

| oxidation | desired product | 14-methyl thio analogue | 14-chloro analogue | the other impurities |
|---|---|---|---|---|
| AZADO oxidization (Ex. 1) | 99.1% | ND | ND | 0.86% |
| Swern oxidation (Con Ex. 1) | 88.0% | 3.10% | 0.74% | 8.16% |

ND: Not detected

As shown in the above result, Swern oxidation introduces the generation of 14-methylthio and 14-chloro compounds. Those impurities are difficult to be removed by silica gel column chromatography and may decrease the purity of the final product. In contrast, those impurities are not generated by AZADO oxidation. That is, products with high purity can be obtained.

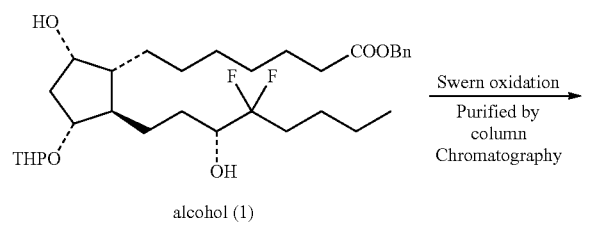

alcohol (1)

Swern oxidation
Purified by column
Chromatography

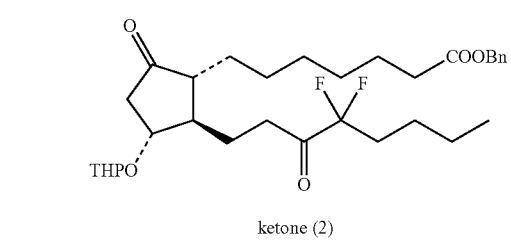

ketone (2)

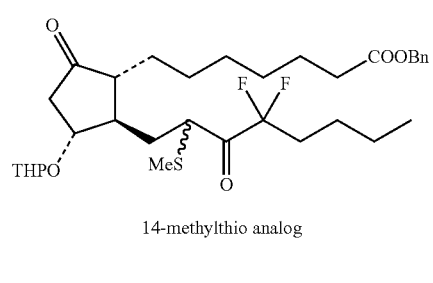

14-methylthio analog

14-chloro analog

What is claimed is:

1. A method for manufacturing a fatty acid derivative represented by formula (I):

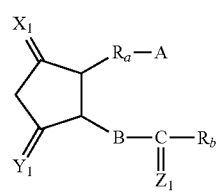

wherein $X_1$ is

wherein R1 is a protecting group for hydroxy group;

$Y_1$ is

wherein R2 is a protecting group for hydroxy group;

$Z_1$ is

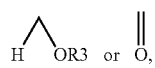

wherein R3 is a protecting group for hydroxy group, provided that at least one of $X_1$, $Y_1$ and $Z_1$ is $$\underset{O}{\|}\;;$$

A is —CH$_3$, —CH$_2$OH, —COCH$_2$OH, —COOH or a salt, ether, ester or amide thereof;

B is a single bond, —CH$_2$—, —CH$_2$—CH$_2$—, —CH=CH— or —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Ra is bivalent saturated or unsaturated lower-medium aliphatic hydrocarbon group, which is unsubstituted or substituted by halogen atom, lower alkyl, lower alkoxy, oxo, aryl or heterocyclic group, provided that one or more carbon atoms of the aliphatic hydrocarbon group may optionally be replaced with oxygen, nitrogen or sulfur atom; and Rb is hydrogen atom; saturated or unsaturated lower-medium aliphatic hydrocarbon group which is unsubstituted or substituted by a halogen, oxo, hydroxy, lower alkoxy, lower alkanoyloxy, cyclo(lower)alkyl, cyclo(lower)alkyloxy, aryl, aryloxy, heterocyclic or heterocyclic oxy;

cyclo(lower)alkyl; cyclo(lower)alkyloxy; aryl; aryloxy; heterocyclic; or heterocyclic oxy, which comprises the step of, reacting a compound of formula (II):

(II)

wherein, $X_2$ is the same as $X_1$ except for when $X_1$ is $$\|_O,$$

$X_2$ is $$H\overset{}{\diagup}\underset{OH}{} \text{ or } \|_O,$$

$Y_2$ is the same as $Y_1$ except for when $Y_1$ is $$\|_O,$$

$Y_2$ is $$H\overset{}{\diagup}\underset{OH}{} \text{ or } \|_O;$$

$Z_2$ is the same as $Z_1$ except for when $Z_1$ is $$\|_O,$$

$Z_2$ is $$H\overset{}{\diagup}\underset{OH}{} \text{ or } \|_O,$$

provided that at least one of $X_2$, $Y_2$ and $Z_2$ is $$H\overset{}{\diagup}\underset{OH}{};$$

and, A, B, Ra and Rb are the same as above;
with a co-oxidizer under the presence of an azaadamantane-N-oxyl compound.

2. The method of claim 1, wherein A is —COOH or a salt, ester or amide thereof.

3. The method of claim 1, wherein the azaadamantane-N-oxyl compound is 2-azaadamantane-N-oxyl.

4. The method of claim 1, wherein the azaadamantane-N-oxyl compound is 1-methyl-2-azaadamantane-N-oxyl.

5. The method of claim 1, wherein the azaadamantane-N-oxyl compound is 2-hydroxy-2-azaadamantane.

6. The method of claim 1, wherein the azaadamantane-N-oxyl compound is 2-hydroxy-1-methyl-2-azaadamantane.

* * * * *